United States Patent [19]

Momose

[11] Patent Number: 5,715,291
[45] Date of Patent: Feb. 3, 1998

[54] PHASE-CONTRAST X-RAY CT APPARATUS

[75] Inventor: Atsushi Momose, Saitama-ken, Japan

[73] Assignee: Hitachi, Ltd., Tokyo, Japan

[21] Appl. No.: 780,572

[22] Filed: Jan. 8, 1997

[30] Foreign Application Priority Data

Jan. 10, 1996 [JP] Japan .................. 8-002048
[51] Int. Cl.$^6$ .................................... G21K 1/06
[52] U.S. Cl. ................... 378/84; 378/4; 378/70
[58] Field of Search .................. 378/4, 62, 21, 378/70, 71, 74, 84

[56] References Cited

U.S. PATENT DOCUMENTS

| 5,173,928 | 12/1992 | Momose et al. ............... 378/4 |
| 5,259,013 | 11/1993 | Kuriyama et al. ............ 378/43 |

FOREIGN PATENT DOCUMENTS

| 0466047A2 | 1/1992 | European Pat. Off. ....... G01N 23/04 |
| 0539608A1 | 5/1993 | European Pat. Off. ....... G01N 23/04 |
| WO9505725 | 2/1995 | WIPO . |

OTHER PUBLICATIONS

A. Momose, et al., Rev. Sci. Instrum. 66 (2), Feb. 1995, pp. 1434–1436.

Nuclear Instruments & Methods in Physics Research, A 352 (1995), pp. 622–628, A. Momose.

T.J. Davis, D. Gao, T.E. Gureyev, A.W. Stevenson and S.W. Wilkins, Phase–Contrast Imaging of Weakly Absorbing Materials Using Hard X–Rays, Letters to Nature, vol. 373, Feb. 16, 1995, pp. 595–597.

T.J. Davis and A.W. Stevenson, Direct Measure of the Phase Shift of An X-Ray Beam, Journal of Optical Society of America, vol. 13, No. 6, Jun. 1996, pp. 1193–1198.

*Primary Examiner*—Don Wong
*Attorney, Agent, or Firm*—Kenyon & Kenyon

[57] ABSTRACT

A phase-contrast X-ray CT apparatus is provided with an X-ray source for generating an X-ray beam, a crystal for generating a diffracted beam by irradiation with the X-ray beam, an object arranging section provided in the direction of propagation of the diffracted beam so that it is rotatable relative to the diffracted beam, an analyzer crystal for receiving a beam transmitted through the object arranging section to extract only a specified refraction angle component, and a sensor for detecting a beam extracted by the analyzer crystal.

8 Claims, 6 Drawing Sheets

PHASE-CONTRAST X-RAY CT APPARATUS

BACKGROUND OF THE INVENTION

The present invention relates to non-destructive and three-dimensional observation of the inside of an object using X-rays, and more particularly to such observation for an object made of light elements to which the conventional method relying on absorption contrast has a poor sensitivity. The present invention is applicable to inspection instruments for organic materials or medical diagnosis apparatuses.

In the conventional X-ray transmission imaging system, the contrast of an obtained image depends upon the degree of absorption of X-rays by an object. Namely, if there is a region where heavy elements with high X-ray absorptance are dense, that portion exhibits a low transmittance and can be caught as a shadow in a image. Reversely, an organic matter made of light elements is transparent to X-rays and is therefore difficult to obtain an image contrast. Accordingly, there is employed a method in which the contrast is emphasized by injecting heavy elements as a contrast agent in order to observe biological soft tissues (such as internal organs, tumors, or blood vessels), for example, when an X-ray cross section image for medical diagnosis is to be acquired. However, it is not always that the contrasting (or emphasizing) technique can be applied to all of observation locations to be investigated. Also, there may be the case where the contrasting process gives a bad influence on the body. The above problem concerning the image contrast exists similarly even in X-ray CT (Computerized Tomography) which is a three-dimensional inside observing technique.

On the other hand, there is an imaging method which depends upon not the absorption of X-rays but phase contrast. Since the X-ray phase shift cross section for light elements is about one-thousand times as large as the interaction cross section of X-ray absorption, the use of the phase-contrast imaging method enables observation with an excellent sensitivity which is one-thousand times as high as that in the conventional imaging method. This shows that biological soft tissues can be observed without being subjected to a specific contrasting process. This is experimentally testified. Also, even if a contrast agent is used, the choice of a wider variety of contrast agents and contrasting techniques is possible. This facilitates to cope with specified purposes such as function imaging.

As a technique much relevant to the present invention, there has been devised a phase-contrast X-ray CT apparatus in which phase contrast is introduced to the X-ray CT enabling three-dimensional observation. The system construction thereof is disclosed by U.S. Pat. No. 5,173,928 to A. Momose et al., and the examples of observation of biological tissues are disclosed by A. Momose, et al., ReV. Sci. Instrum. 66 (1995) 1434. According to the disclosed technique, an X-ray interferometer is used to reconstruct an image in a virtual cross section from interference patterns. The examples of observation are shown for an object having a diameter of several millimeters. However, the disclosed technique reaches no practisation to medical diagnosis.

SUMMARY OF THE INVENTION

An object of the present invention is to provide a phase-contrast X-ray CT with a simple system which uses no X-ray interferometer. The above-mentioned system using the X-ray interferometer has a problem (1) that in order to ensure coherency, the energy band of an X-ray beam must be narrowed to obtain a high monochromaticity and hence a bright light source such as synchrotron radiation must be used, a problem (2) that a precision optical system is required and it is therefore difficult to handle the system, and a problem (3) that a technique for ensuring a wide field of view counterbalancing the practical use is not established.

The X-ray CT based on phase contrast requires the phase distribution of X-rays as input data. In the above-mentioned method using the X-ray interferometer, the phase distribution is acquired by an operation from interference patterns. In a technique of the present invention, on the other hand, no X-ray interferometer is used and the phase distribution is determined by the following method.

Namely, as shown in FIG. 1, an object 1 is irradiated with X-rays 2. It is assumed that the object 1 does not exhibit strong X-ray absorption (Image contrast is not created from absorption.) and transmitted X-rays 3 are obtained. It is also assumed that due to a phase shift caused by the object 1, the wavefront 2' of X-rays 2 (herein assumed as a plane wave, for simplicity) changes, as shown by the wavefront 3' of X-rays 3. Since the phase shift $\phi(x)$ corresponds to the amount of change in wavefront form, the measurement of the phase shift $\phi(x)$ corresponds to the measurement of the wavefront form. The following discussion will be made with an attention to the wavefront form on an x-axis for simplicity but will be expanded to a discussion on an x-y plane later on.

If the intensity distribution of X-rays is only measured, information concerning the wavefront form (or phase information) is lost. In the above-mentioned method using the X-ray interferometer, the wavefront form is determined from an interference pattern generated by superimposing reference X-rays on X-rays transmitted through an object. In the present invention, on the other hand, an analyzer crystal 4 (see FIG. 1) is used to determine the wavefront form. Since an X-ray beam propagates in a direction normal to the wavefront thereof, a bend of the wavefront as shown in FIG. 1 may be understood as a change in propagation direction by the refraction of the beam. In the case of FIG. 1, therefore, the propagation direction is delicately different at points A, B and C in accordance with the gradients of the wavefront. Now assume that the analyzer crystal 4 is set so that an incidence angle for X-rays at the point A satisfies the Bragg diffraction condition. It is also assumed that the diffraction index of the analyzer crystal 4 is selected to provide a sufficiently narrow diffraction angle width and X-rays at the points B and C are not reflected by the analyzer crystal 4. In this case, only X-rays at the point A and X-rays substantially parallel thereto will be detected at the position of an X-ray image sensor 6. Namely, the analyzer crystal 4 has a function of selecting only a certain specified gradient portion of the wavefront 3'. The foregoing discussion is described by WO 95/05725 "IMPROVED X-RAY OPTICS, ESPECIALLY FOR PHASE CONTRAST IMAGING". However, this reference is silent about a method for determining the phase distribution. Accordingly, a new invention must be added for combination with the technique of X-ray CT. In the present invention, the phase distribution is determined as follows.

Provided that the refraction angle θ of the beam and a phase shift $\phi$ caused by the object 1, satisfies the relation of $$\theta(x) = \lambda \frac{\partial \phi}{\partial x} \tag{1}$$

where λ is the wavelength of X-rays. From equation (1), there is obtained $$\phi = \frac{1}{\lambda} \int \theta(x) dx \qquad (2)$$

Namely, it is indicated that φ can be determined by examining the refraction angle θ at each point x of an image and integrating θ with respect to x. This is a phase distribution which is to be determined. Thus, the distribution of refraction angles is determined in such a manner that the analyzer crystal 4 is adapted to rotate around a certain rotation axis 5 at a high precision to record the diffraction intensity by the X-ray image sensor 6 plural times while changing the setting angle of the analyzer crystal 4 and the setting angle providing the maximum diffraction intensity is examined for each pixel. As shown by equation (2), a phase distribution is determined by integrating the obtained diffraction distribution. Also, it is possible to determine the zero point of φ at a portion where there is no object in the image.

Since the refraction angle of X-rays is of order several seconds at the largest, the blur of the image caused by this refraction is several-ten μm even if a distance between the object and the X-ray image sensor is of order 1 m. Accordingly, if image observation with a more coarse spatial resolution than that is premised, there is no problem.

In order to reconstruct a CT image, the intact use of the conventional algorithm is possible for φ in a plurality of projection directions collected by rotating the object or by rotating the X-ray source, the analyzer crystal and the X-ray image sensor in an integral manner.

Next, the discussion will be shown in conjunction with the case where the wavefront is considered as being in two dimensions. The refraction angle θ at each point can be represented by $$\theta = (\theta_x, \theta_y) \qquad (3)$$

or in two refraction directions which are orthogonal to each other. The refraction angles in the two directions can be written, respectively, as $$\left. \begin{array}{l} \theta_x(x) = \lambda \frac{\partial \phi}{\partial x} \\ \theta_y(y) = \lambda \frac{\partial \phi}{\partial y} \end{array} \right\} \qquad (4)$$

Namely, $$\left. \begin{array}{l} \phi = \frac{1}{\lambda} \int \theta_x(x) dx \\ \phi = \frac{1}{\lambda} \int \theta_y(y) dy \end{array} \right\} \qquad (5)$$

are also satisfied. Accordingly, that at least one of $\theta_x$ and $\theta_y$ is known, suffices in order to determine φ. Therefore, the analyzer crystal 4 may be scanned in either x-axis direction or y-axis direction. Now assume that the rotation axis of the analyzer crystal 4 is parallel to the y-axis and the refraction angle in the x-axis direction is examined. Since the refraction in the y-axis direction at this time gives little influence on the diffraction condition of the analyzer crystal 4, it is possible to determine $\theta_x$ independently. The difference of the present invention from the known phase-contrast X-ray CT lies in that a system for determining data φ inputted to a CT image reconstruction algorithm is facilitated, thereby improving the practicability. In other words, the present invention provides a merit that there is not needed an X-ray interferometer which is difficult to fabricate and handle, a merit that a thick X-ray beam can be used, thereby making it possible to ensure a wide field of view, and a merit that it is possible to structure a relatively bright optical system. Namely, the present has features which are advantageous when viewed from medical applications.

The precision of phase determination depends upon the precision of refraction angle determination. The refraction angle of order 0.01 seconds is regarded as being a detection limit in the present invention. If an X-ray interferometer is used so that a beam having a similar refraction angle is subjected to interference with a reference X-ray beam, interference fringes are generated at the intervals of about 2 mm with X-rays of about 1 Å. Even in the case where the refraction is more gentle, the interference fringes can be detected easily since the intervals of interference fringes are expanded. Namely, it can be said that for weak refraction, the use of the X-ray interferometer offers a high sensitivity rather than not. Reversely, in the case where the refraction becomes large, the intervals of interference fringes are narrowed and the visibility of interference fringes is deteriorated as the intervals of interference gets near the spatial resolution of the X-ray image sensor. Of course, interference fringes having the intervals narrower than the spatial resolution cannot be detected. In the technique of the present invention, on the other hand, larger refraction is detected more easily. Namely, it can be said that the present invention and the phase-contrast X-ray CT using the X-ray interferometer are not necessarily competitive techniques but are different in advantageous sensitivity region. The technique according to the present invention can be regarded as an invention to obtain image in a sensitivity region which is intermediate between those of the conventional X-ray CT relying on absorption contrast and the phase-contrast X-ray CT using the X-ray interferometer.

DESCRIPTION OF THE PREFERRED EMBODIMENTS

Embodiments of the present invention will now be explained using the accompanying drawings.

(EMBODIMENT 1)

Figure 1:
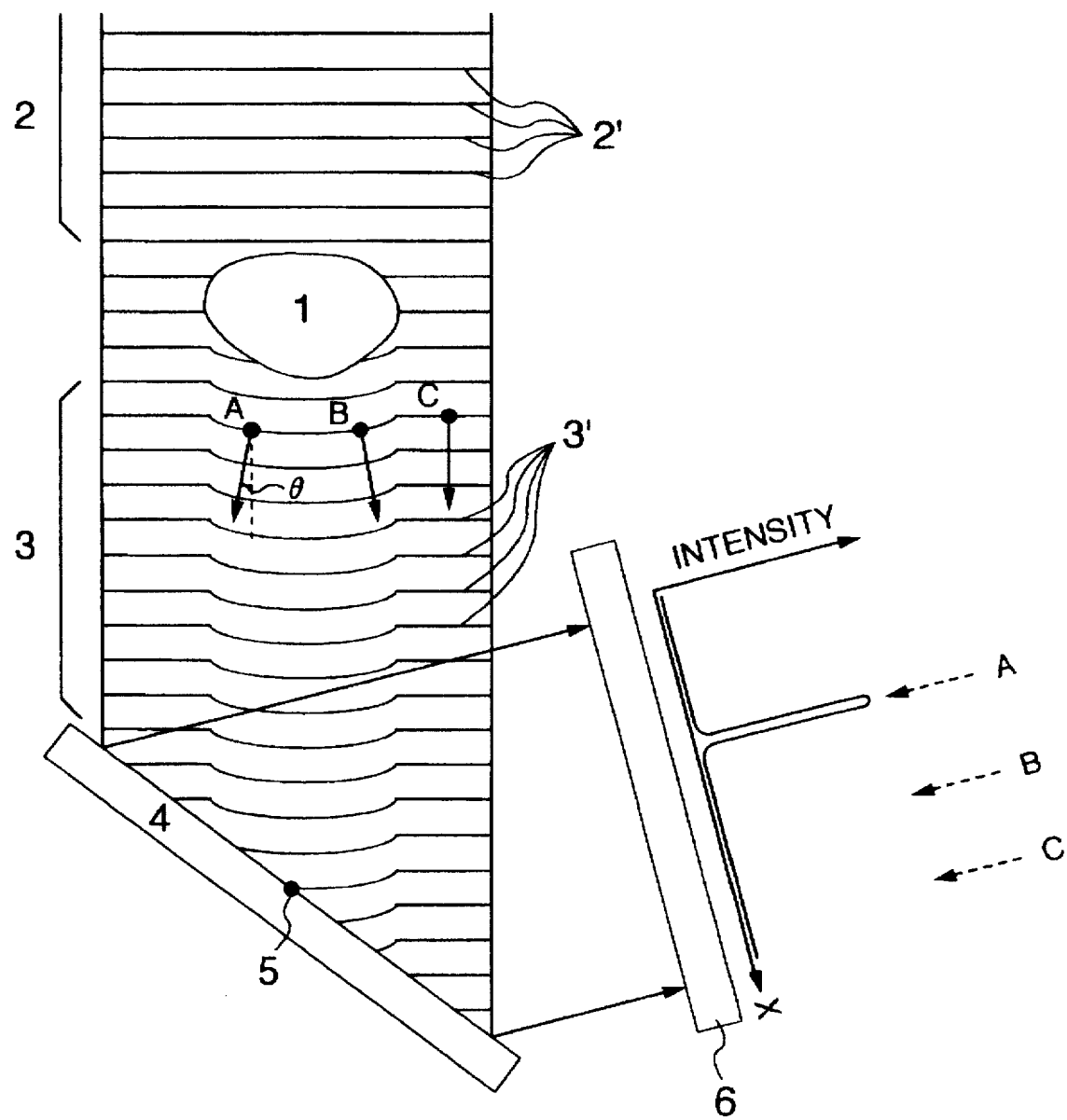
FIG. 1 is a diagram for explaining the principle of a method for determination of a phase shift generated by transmitting X-rays through an object.
Figure 2:
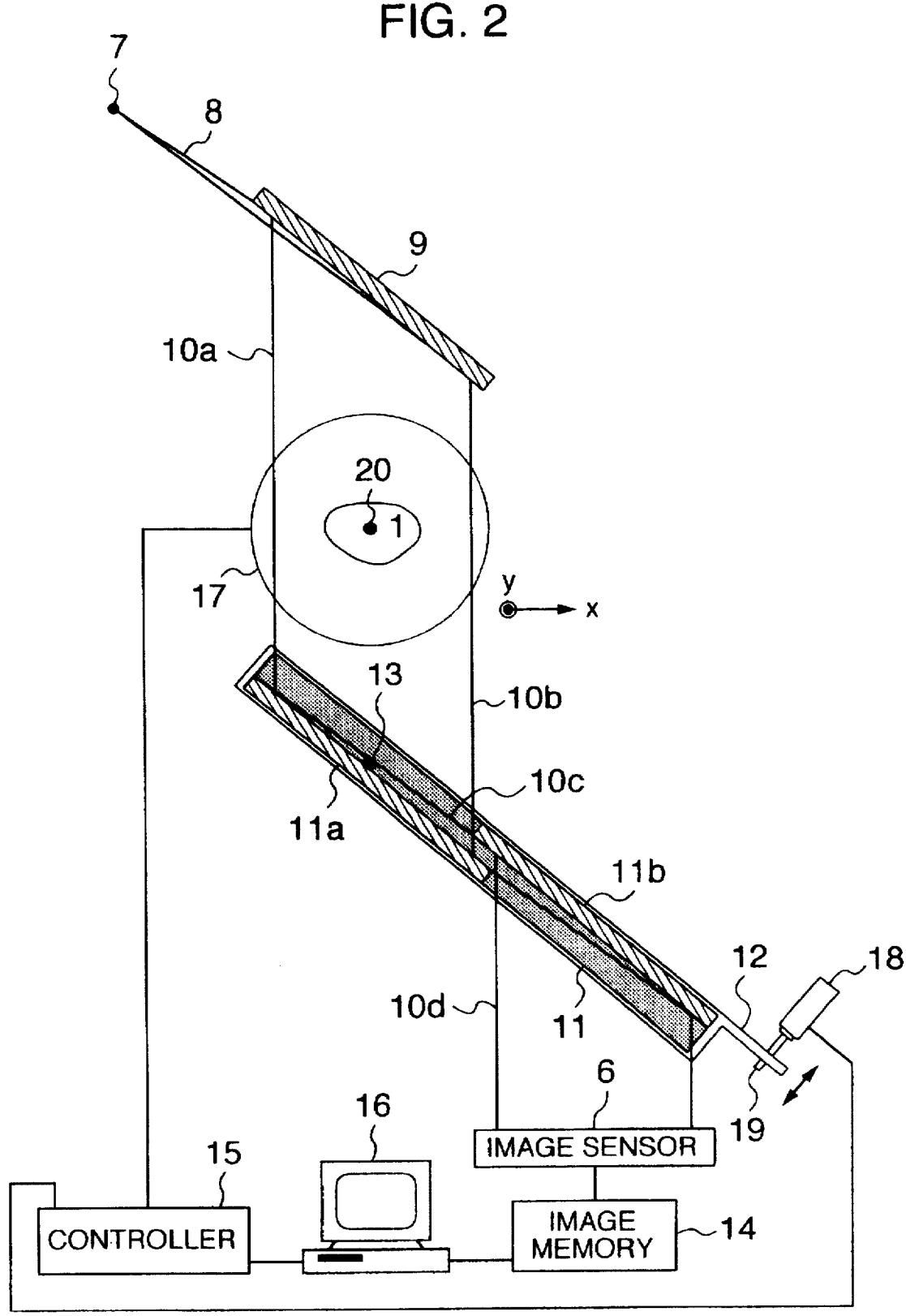
FIG. 2 is a system diagram according to a first embodiment of the present invention.
Figure 3:
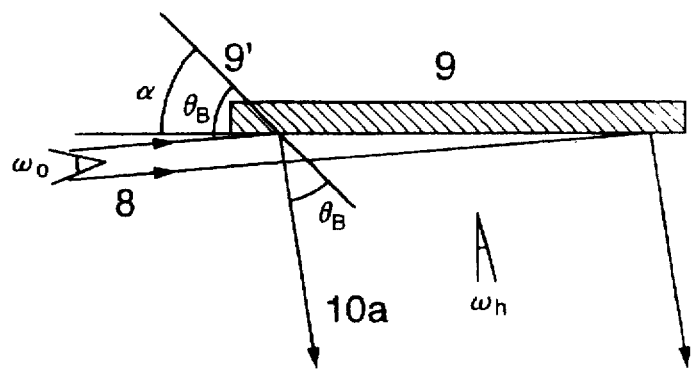
FIG. 3 shows the situation of diffraction in the case where a crystal surface and a crystal lattice plane are inclined with respect to each other.

FIG. 2 shows the construction of a first embodiment of the present invention. A crystal 9 cut from a good-quality perfect crystal ingot such as silicon is irradiated with an X-ray beam 8 obtained from an X-ray source 7. X-rays with a specified energy band satisfying the diffraction condition for a lattice plane 9' (see FIG. 3) inclined with respect to the surface of the crystal 9 generate a diffracted beam 10a. A feature as shown in FIG. 3 is known about the asymmetrical reflection of X-rays by the crystal. Namely, provided that the crystal lattice plane 9' of the crystal 9 is inclined by an angle α with respect to the crystal surface, as shown in FIG. 3, the asymmetry factor b can be defined by $$b = \frac{\sin(\theta_B - \alpha)}{\sin(\theta_B + \alpha)} \quad (6)$$

The width of the beam comes to 1/b times and the divergence angle of the beam comes to b times (that is, $\omega_h/\omega_o=b$). Namely, as the value of α is nearer to the Bragg angle $\theta_B$, the beam width is expanded and the divergence angle of the diffracted beam becomes smaller to approximate a plane wave. Accordingly, the crystal 9 has not only a monochromatizing function of limiting the energy band width of the diffracted beam but also a function of enlarging the cross section of the beam and a function of collimating the diffracted beam (or approximating it to a plane wave).

Only that component of a beam 10b transmitted through the object 1 and subjected to phase shift (or refraction), which has a specified refraction angle, is extracted by an analyzer crystal 11 as a beam 10c. The analyzer crystal 11 utilizes asymmetrical diffraction as in the crystal 9 but has two reflection faces (11a and 11b) in an monolithic block. Also, the diffraction faces of the crystal 9 and the analyzer 11 are approximately parallel to each other. This is because since the collimarion in the x-axis direction is made by the crystal 9 but the beam divergence from the X-ray source 7 remains in the y-axis direction as it is, there is yielded a disadvantage in the aspect of precision even if the determination of the refraction angle is tried with the rotation in the y-axis direction made taking the x-axis of the analyzer 11 as a rotation axis. Further, the incident path of X-rays to the crystal 11a is reverse to that to the crystal 9 in order to provide a high sensitivity even to slight refraction. However, since the spatial width of the diffracted beam 10c becomes narrow, the beam is diffracted by the crystal 11b again (in a manner similar to that by the crystal 9) for restoration to the original beam width. The crystal 11 is fixed on a rotation table 12 and is rotatable, around a point 13 taken as a supporting point at a high precision, by a shaft 19 which a parallel displacement mechanism 18 using a linear motor, piezoelectric element or the like pushes.

A beam 10d passed through the analyzer crystal 11 is detected by the X-ray image sensor 6 and the detected data (or diffraction intensity) is stored into an image memory 14 each time the analyzer crystal 11 is set to a specified angle. In an image processor 16, the setting angle of the analyzer crystal 11 providing the maximum intensity is determined for each pixel of the X-ray image sensor 6 and θ(x) is determined in accordance with equation (4). Since the integrated form of θx is a phase distribution image φ(x), the image processor 16 can determine $\phi_x(x)$ by operation. (The x-axis and y-axis are defined as shown in FIG. 2.)

By rotating a table 17 for the object around an axis 20 for the purpose of CT scan, the phase can be determined in a plurality of projection directions. The rotation of the object 1 and the rotation of the analyzer crystal 11 are made using a controller 15 which can be driven in synchronism with the image processor 16. An equivalent scan can also be performed by rotating the X-ray source 7, the crystal 9, the analyzer crystal 11 and the X-ray image sensor 6 around the axis 20 in a synchronous manner with the object being kept stationary. Thus, a phase distribution image in each projection direction is acquired. A phase-contrast X-ray CT image can be reconstructed by inputting the acquired data to a general X-ray CT algorithm. When the X-ray image sensor 6 is a two-dimensional sensor, three-dimensional observation becomes possible since CT images in a series of plural planes parallel to the drawing sheet surface can be reconstructed in accordance with the above method.

Figure 4:
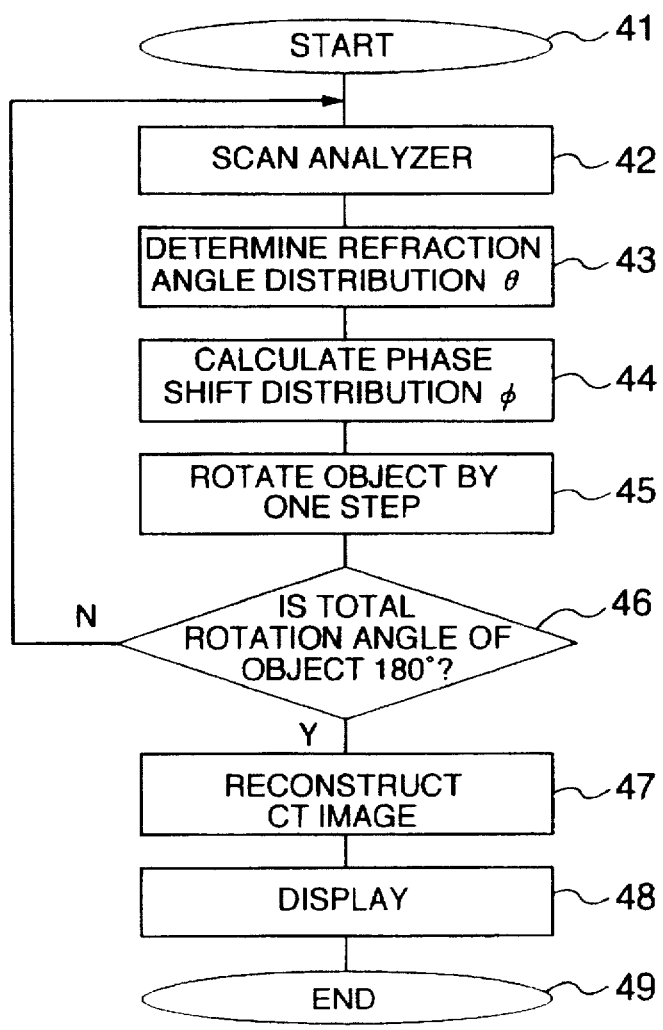
FIG. 4 is a flow chart of measurement.

FIG. 4 shows a flow chart of a series of measurement procedures. The flow starts from step 41. The analyzer is scanned (step 42), a refraction angle distribution θ is determined (step 43), a phase shift distribution φ is calculated (step 44) and the object is rotated by one step (step 45). In step 46, the judgement is made as to whether or not the total rotation angle of the object is 180°. If the result of judgement in step 46 is "NO", the flow returns to step 42. If the result of judgement in step 46 is "YES", a CT image is reconstructed (step 47) and displayed (step 48). The series of measurement procedures are completed by step 49. Though the present invention utilizes the bend of X-rays by refraction, approximation is assumed so that image blur caused by the bend is substantially negligible. Accordingly, the object is scanned by 180° and data of the remaining half round can use an inverted version of data of the first half round. Of course, if it does not matter that the scanning time is doubled, the scan over 360° may be conducted having a preference for the improvement of image quality.

Also, it cannot be said positively that the beam 10a is a plane wave strictly. Accordingly, it is necessary to examine the initial wavefront form (or initial phase value) of the beam 10a by scanning the analyzer 11 beforehand in a state in which there is no object. A phase shift caused by an object corresponds to an amount by which a wavefront form determined with the object inserted changes from the initial wavefront form. There are a method in which phase shifts φ before and after the insertion of an object are determined to produce a difference therebetween, and a method in which a difference in refraction angle distribution is first determined to integrate the difference. Flow charts (of only the corresponding portions) in the respective cases are shown in FIGS. 5A and 5B.

Figure 5A:
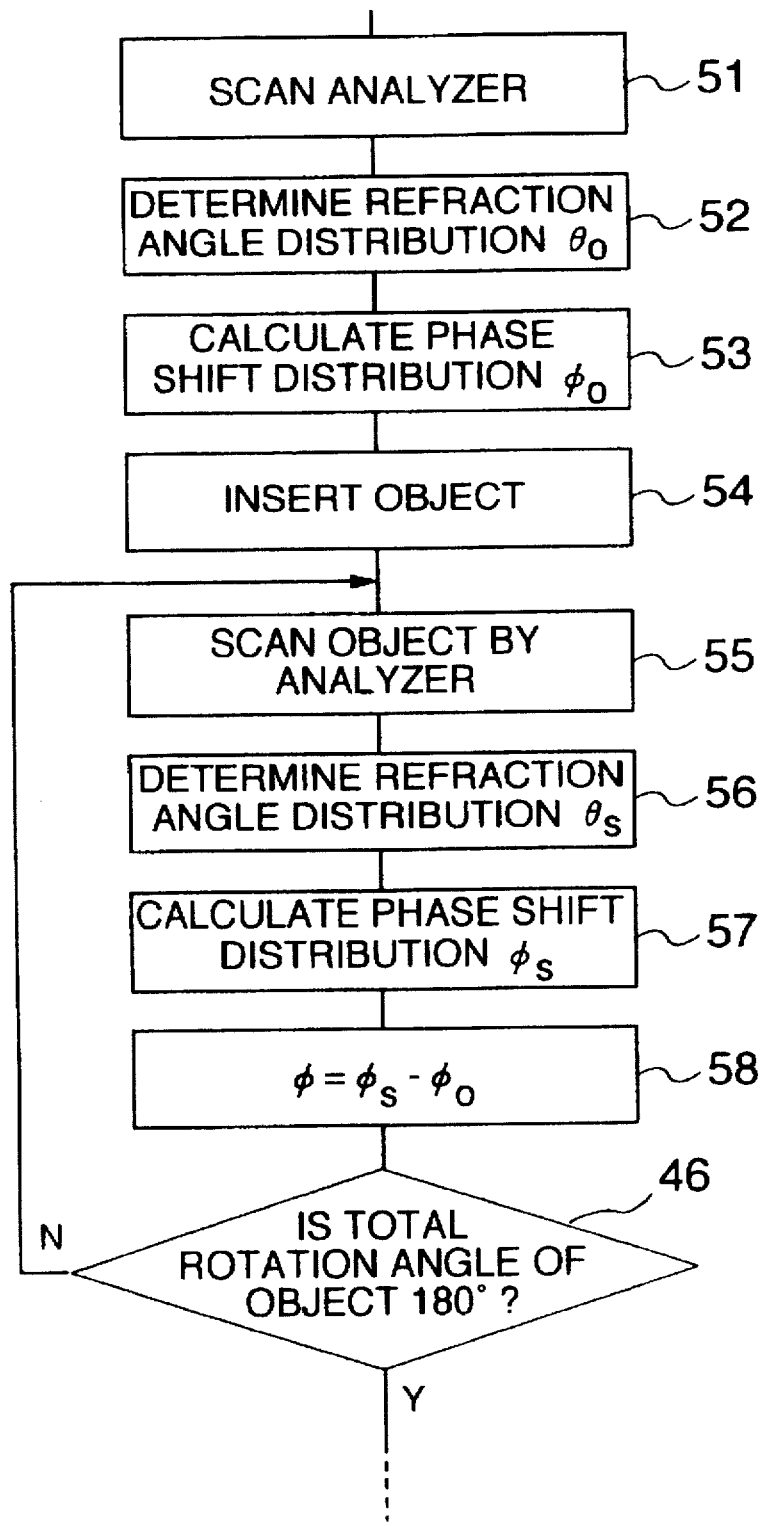
FIG. 5A is a flow chart in the case where an initial phase value is corrected.

In the method shown in FIG. 5A, the analyzer is scanned (step 51), a refraction angle distribution $\theta_o$ is determined (step 52) and a phase shift distribution $\phi_o$ is calculated (step 53). Thereafter, an object is inserted (step 54), the object is scanned by the analyzer (step 55), a refraction angle distribution $\theta_s$ is determined (step 56), a phase shift distribution $\phi_s$ is calculated (step 57) and $\phi=\phi_s=\phi_o$ is determined (step 58).

Figure 5B:
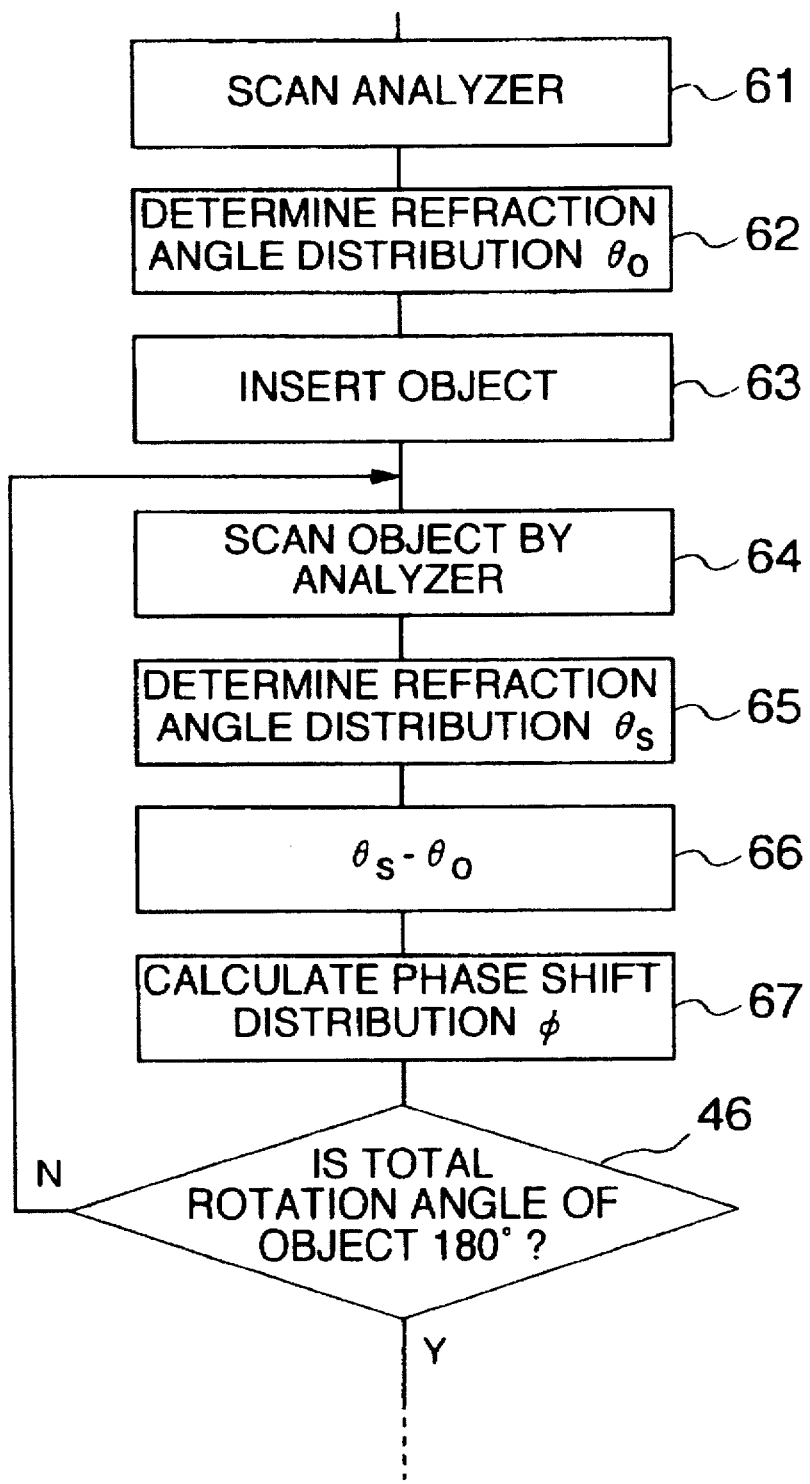
FIG. 5B is another flow chart in the case where the initial phase value is corrected.

In the method shown in FIG. 5B, the analyzer is scanned (step 61), a refraction angle distribution $\theta_o$ is determined (step 62) and an object is inserted (step 63). Thereafter, the object is scanned by the analyzer (step 64), a refraction angle distribution $\theta_s$ is determined (step 65), $\theta_s-\theta_o$ is determined (step 66) and a phase shift distribution φ is calculated (step 67).

(EMBODIMENT 2)

In the first embodiment, the used analyzer crystal has the monolithic configuration of two surfaces which are inclined with respect to a crystal lattice plane. In this case, since diffraction is caused twice, there is some amount of loss in intensity until the beam reaches the image sensor. In a second embodiment of the present invention, there is used an analyzer crystal which relies on higher-order diffraction and has a high angular resolution. In this analyzer crystal, the diffraction is caused once.

Figure 6:
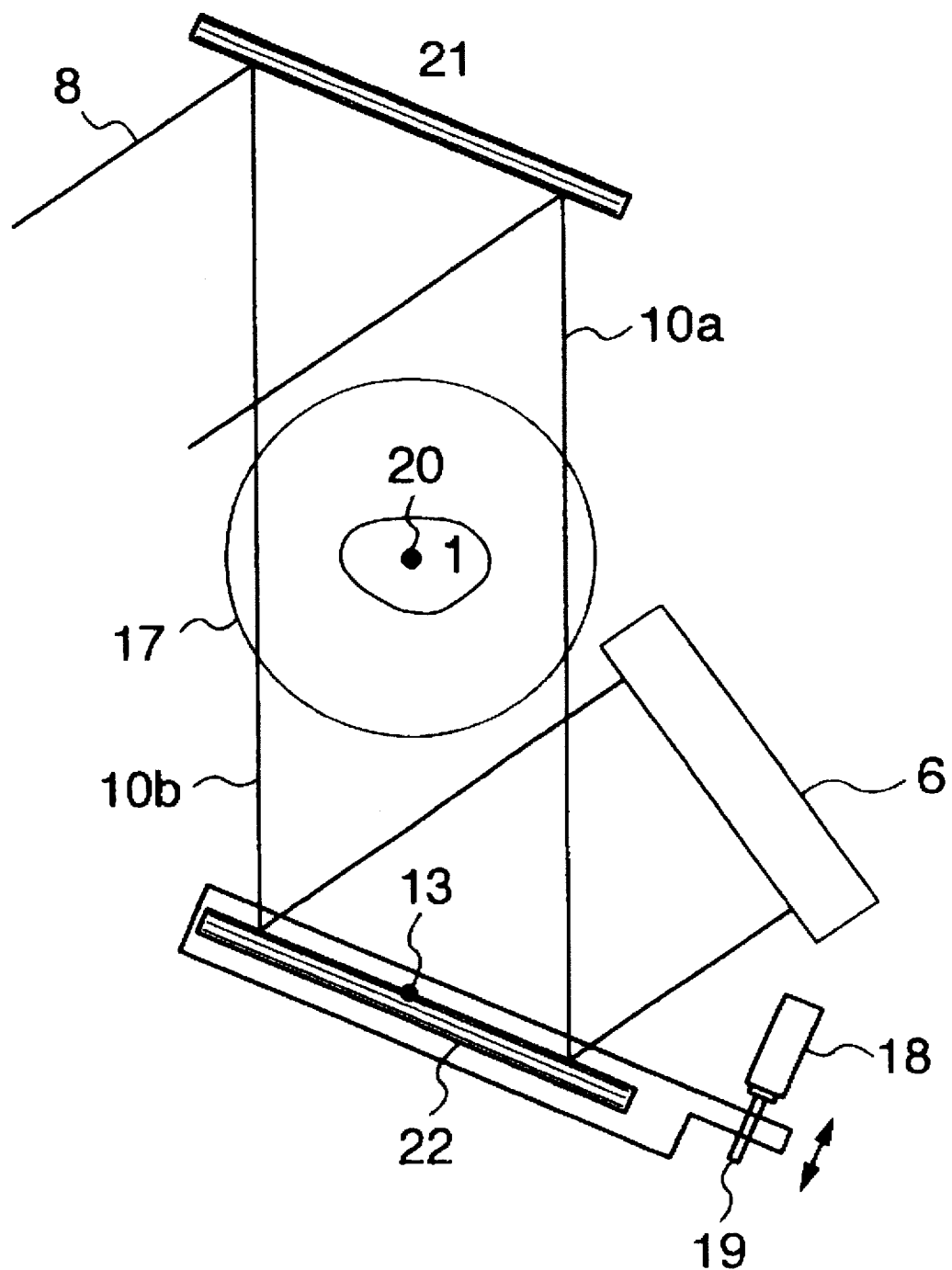
FIG. 6 is a system diagram according to a second embodiment of the present invention.

The construction of the second embodiment is shown in FIG. 6. Crystals 21 and 22 are different from the crystals in the first embodiment. The crystal 21 is provided for the same purpose as that of the crystal 9 in the first embodiment. Therefore, the same as the crystal 9 in the first embodiment can be disposed as the crystal 21. The crystal 22 uses a symmetrical reflection plane in order to prevent the image of an object 1 from being demagnified. The other construction is the same as that of the first embodiment. When higher-order diffraction is used, there may be a demerit that an insertion space for the object 1 is narrowed since a diffraction angle becomes large.

According to the present invention, three-dimensional observation based on X-ray phase contrast becomes possible with a relatively simple system construction. Also, it is possible to ensure a wide field of view easily, thereby facilitating the application to an object which is larger than that to which the system using an X-ray interferometer is applied.

What is claimed is:

1. A phase-contrast X-ray CT apparatus in which an object is irradiated with X-rays from a plurality of different directions and a tomogram of the object is reconstructed from an X-ray phase shift distribution generated when the X-rays transmit through the object, wherein said phase shift distribution is determined from the distribution of refraction angles of X-rays transmitted through said object.

2. A phase-contrast X-ray CT apparatus according to claim 1, wherein in order to examine the distribution of refraction angles of X-rays transmitted through said object, an X-ray beam transmitted through said object is subjected to diffraction by a crystal disposed in rear of said object, a plurality of diffraction images are acquired by a two-dimensional or one-dimensional X-ray sensor while changing the incidence angle of said X-ray beam onto said crystal, and said phase shift distribution is determined by an operation from the plurality of acquired diffraction images.

3. A phase-contrast X-ray CT apparatus according to claim 2, wherein in acquiring the diffraction images while changing the incidence angle of said X-ray beam onto said crystal, an angular position providing the maximum X-ray intensity is determined at each pixel position of the image and a phase shift distribution image is acquired from an image in which said angular position is arranged for each pixel.

4. A phase-contrast X-ray CT apparatus wherein a tomogram of an object is reconstructed from an X-ray phase shift distribution, said apparatus comprising:

an X-ray source for generating an X-ray beam;

a first crystal for generating a diffracted beam by irradiation with said X-ray beam;

an object arranging section provided in the direction of propagation of said diffracted beam;

a second crystal for receiving the X-ray beam transmitted through said object arranging section to extract X-ray components having different refraction angles; and a sensor receiving said X-ray components from said second crystal and detecting a distribution of refraction angles of said X-ray beam to determine a phase shift distribution of said X-ray beam on the basis of the detected distribution of refraction angles of said X-ray beam.

5. A phase-contrast X-ray CT apparatus according to claim 4, further comprising a mechanism for rotating the diffracted beam from said first crystal and said object arranging section relative to each other.

6. A phase-contrast X-ray CT apparatus according to claim 4, further comprising a mechanism for rotating said second crystal with one point taken as a supporting point.

7. A phase-contrast X-ray CT apparatus according to claim 4, wherein said second crystal includes a first crystal portion for causing the diffraction of the beam transmitted through said object arranging section and a second crystal portion for causing the diffraction of the diffracted beam from said first crystal portion again.

8. A phase-contrast X-ray CT apparatus wherein a tomogram of an object is reconstructed from an X-ray phase shift distribution, said apparatus comprising:

an X-ray source for generating an X-ray beam;

a first crystal for generating a diffracted beam by irradiation with said X-ray beam;

an object arranging section provided in the direction of propagation of said diffracted beam;

a second crystal for receiving the X-ray beam transmitted through said object arranging section to extract only a component having a specific refraction angle of the X-ray beam;

a scanner for changing an angle of said second crystal with respect to the object for extracting components having different refraction angles of the X-ray beam from said second crystal; and a sensor receiving said X-ray beam from said second crystal and detecting a distribution of refraction angles of said X-ray beam to determine a phase shift distribution of said X-ray beam on the basis of the detected distribution of refraction angles of said X-ray beam.

* * * * *